US010080916B2

(12) United States Patent
Lee

(10) Patent No.: US 10,080,916 B2
(45) Date of Patent: Sep. 25, 2018

(54) FITNESS STRUCTURE

(71) Applicant: Ki Won Lee, Seoul (KR)

(72) Inventor: Ki Won Lee, Seoul (KR)

( * ) Notice: Subject to any disclaimer, the term of this patent is extended or adjusted under 35 U.S.C. 154(b) by 0 days.

(21) Appl. No.: 15/086,670

(22) Filed: Mar. 31, 2016

(65) Prior Publication Data

US 2017/0282002 A1    Oct. 5, 2017

(51) Int. Cl.
| | | |
|---|---|---|
| *A63B 21/062* | (2006.01) | |
| *A63B 21/00* | (2006.01) | |
| *A63B 23/12* | (2006.01) | |
| *A61B 5/00* | (2006.01) | |
| *A63B 71/06* | (2006.01) | |
| *A63B 23/035* | (2006.01) | |
| *A63B 21/008* | (2006.01) | |
| *A63B 21/055* | (2006.01) | |
| *A63B 23/04* | (2006.01) | |
| *A63B 71/00* | (2006.01) | |

(52) U.S. Cl.
CPC ............ *A63B 21/0626* (2015.10); *A61B 5/00* (2013.01); *A63B 21/062* (2013.01); *A63B 21/063* (2015.10); *A63B 21/154* (2013.01); *A63B 23/03525* (2013.01); *A63B 23/1209* (2013.01); *A63B 71/0619* (2013.01); *A63B 21/008* (2013.01); *A63B 21/00061* (2013.01); *A63B 21/00065* (2013.01); *A63B 21/0085* (2013.01); *A63B 21/0552* (2013.01); *A63B 21/4035* (2015.10); *A63B 21/4043* (2015.10); *A63B 2023/0411* (2013.01); *A63B 2071/0063* (2013.01); *A63B 2071/0625* (2013.01); *A63B 2220/10* (2013.01); *A63B 2220/17* (2013.01); *A63B 2220/20* (2013.01); *A63B 2220/30* (2013.01); *A63B 2220/40* (2013.01); *A63B 2220/52* (2013.01); *A63B 2220/808* (2013.01); *A63B 2220/89* (2013.01); *A63B 2225/093* (2013.01); *A63B 2225/15* (2013.01)

(58) Field of Classification Search
CPC .......... A63B 21/062; A63B 21/0626–21/0632; A63B 21/154–21/156; A63B 21/078–21/0783; A63B 21/0624; A63B 21/072–21/075
See application file for complete search history.

(56) References Cited

U.S. PATENT DOCUMENTS

| | | | | |
|---|---|---|---|---|
| 4,286,782 A | * | 9/1981 | Fuhrhop | A63B 21/078 482/103 |
| 4,471,956 A | * | 9/1984 | Marlo | A63B 21/4029 482/104 |

(Continued)

*Primary Examiner* — Gregory Winter
(74) *Attorney, Agent, or Firm* — Novick, Kim & Lee, PLLC; Sang Ho Lee

(57) ABSTRACT

A fitness structure includes a bar having a first end portion and a second end portion, a pair of bar support portions provided at each side of the bar and having a plurality of bar support members to place the bar at a plurality of heights, a first load portion and a second load portion spaced apart from the bar to a certain degree and facing each other, a first cable coupled between the first end portion of the bar and the first load portion, a second cable coupled between the second end portion of the bar and the second load portion. Heights of the first load portion and the second load portion vary depending on a height of one of the plurality of bar support members at which the bar is detachably placed.

20 Claims, 14 Drawing Sheets

(56) References Cited

U.S. PATENT DOCUMENTS

| | | | | |
|---|---|---|---|---|
| 4,856,773 A * | 8/1989 | Deola | ............... | A63B 21/0628 482/102 |
| 5,135,453 A * | 8/1992 | Sollenberger | ........ | A63B 21/155 482/101 |
| 5,655,997 A * | 8/1997 | Greenberg | ......... | A63B 21/0628 482/1 |
| 5,725,459 A * | 3/1998 | Rexach | ............. | A63B 21/0628 482/102 |
| 6,379,287 B1 * | 4/2002 | Slawinski | ........ | A63B 21/00181 482/104 |
| 7,651,443 B1 * | 1/2010 | Fenster | ............... | A63B 23/035 482/103 |
| 9,272,179 B2 * | 3/2016 | Lemos | .................. | A63B 21/06 |
| 2007/0161468 A1 * | 7/2007 | Yanagisawa | ....... | A63B 21/0628 482/94 |

\* cited by examiner

FITNESS STRUCTURE

BACKGROUND

Field of the Disclosure

The present invention relates to an apparatus, and more particularly, to a fitness structure.

Discussion of Related Art

Recently, as a social interest on beauty and health increases, the health population that keeps weight training to improve muscle strength and form a balanced body has increased. Weight training is an exercise to train muscles using an object having a weight such as a barbell or dumbbells, thereby improving physical strength.

Motions used for weight training include the bench press, the squat, the dead lift, etc. A fitness club has various fitness equipment to implement the above various motions.

Fitness equipment for weight training may be divided into free weight exercise and machine exercise. Free weight exercise is an exercise using a barbell and dumbbells, which is very effective for improving body balance using balanced muscles and accessory muscles. Machine exercise is an exercise using fitness equipment including a combination of a weight and a pulley, without a barbell, which makes the exercise easy.

SUMMARY

The present inventive concept provides a fitness structure having improved space usability and enabling various exercises with a single structure.

Additional aspects will be set forth in part in the description which follows and, in part, will be apparent from the description, or may be learned by practice of the presented embodiments.

According to one or more embodiments, a fitness structure includes a bar, a pair of bar support portions provided at one side of the bar and having one or more bar support members to place the bar at a plurality of heights, a first load portion and a second load portion spaced apart from the bar to a certain degree and facing each other, a first cable coupled between one end portion of the bar and the first load portion, and a second cable coupled between the other end portion of the bar and the second load portion, in which heights of the first load portion and the second load portion vary depending on a height of the bar, and even when the first load portion and the second load portion are placed on any one of the plurality of bar support members, one or more weight portions are attachable and detachable with respect to the first load portion and the second load portion.

In a state in which the bar placed on the bar support portion is detached from the bar support portion and held by a user, the bar may be capable of performing a downward motion in the direction of gravity.

The fitness structure may further include a bar accommodation portion formed in a lower portion of the bar support portion and accommodating the bar, and, in a state in which the bar is accommodated in the bar support portion, the bar is capable of performing an upward motion in a direction opposite to gravity.

The one or more weight portions may be detachably provided on the first load portion and the second load portion, regardless of positions of the first load portion and the second load portion.

An insertion hole may be formed in the bar support portion at each of a plurality of heights, each of the plurality of bar support members may be inserted into the insertion hole, and the bar may be supported by the plurality of bar support members.

As the bar is supported by the plurality of bar support members, even when the bar are supported on any one of the plurality of bar support members, the one or more weight portions may be detachably provided to the first load portion and the second load portion.

The first load portion and the second load portion may be moved in a same direction as a movement direction of the bar in a third direction (Z axis).

When the bar is moved in a direction ascending from the ground, the first load portion or the second load portion may be ascended in a vertical direction by the first cable and the second cable connected to the bar.

A movement distance of the bar in the third direction (Z axis) may be longer than a movement distance of the first load portion or the second load portion in the third direction (Z axis).

A distance sensor measuring a movement distance of the first load portion or the second load portion may be further provided on the first load portion or the second load portion.

Each of the first load portion and the second load portion may include a guide portion extending in one direction, an elevation portion elevating along the guide portion, and a weight coupling portion protruding from the guide portion to allow one or more weight portions to be coupled to the weight coupling portion.

The weight coupling portion of the first load portion and the weight coupling portion of the second load portion may protrude in directions facing each other.

The fitness structure may further include a frame on which the first load portion, the second load portion, the first cable, and the second cable are provided and having an inner space formed in the frame, in which one or more weight support portions on which the one or more weight portions are supported is formed on the frame, and the one or more weight support portions protrude from the frame inwardly toward the inner space of the frame.

One or more pulleys may be formed on the frame, the first cable, the first load portion, and the one or more pulleys constitute a pulley system, and the second cable, the second load portion, and the one or more pulleys constitute a pulley system.

A user may be positioned between the first cable and the second cable.

According to one or more embodiments, a fitness structure includes a bar, a first cable coupled to one end portion of the bar, a second cable coupled to the other end portion of the bar, and one or more load portions connected to the first cable or the second cable and applying a certain load to the bar, in which the load portion comprises the first load portion and the second load portion, which are at one side of the bar to face each other, each of the first load portion and the second load portion includes a guide portion extending in one direction, an elevation portion elevating along the guide portion, and a weight coupling portion protruding from the guide portion to allow one or more weight portions to be coupled to the weight coupling portion, and the weight coupling portion of the first load portion and the weight coupling portion of the second load portion protrude in directions facing each other.

The load portion may be moved in a same direction as a movement direction of the bar in a third direction (Z axis).

When the bar is moved in a direction ascending from the ground, the load portion may be ascended in a vertical direction by the first cable and the second cable connected to the bar.

A movement distance of the bar in the third direction (Z axis) may be longer than a movement distance of the load portion in the third direction (Z axis).

The one or more weight portions may be coupled to the weight coupling portion of the first load portion or the second load portion, regardless of a position of the first load portion or the second load portion.

The fitness structure may further include a frame on which the first load portion, the second load portion, the first cable, and the second cable are provided and having an inner space formed in the frame, in which one or more weight support portions on which the one or more weight portions are supported is formed on the frame, and the one or more weight support portions protrude from the frame inwardly toward the inner space of the frame.

One or more pulleys may be formed on the frame, the first cable, the first load portion, and the one or more pulleys constitute a pulley system, and the second cable, the second load portion, and the one or more pulleys constitute a pulley system.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
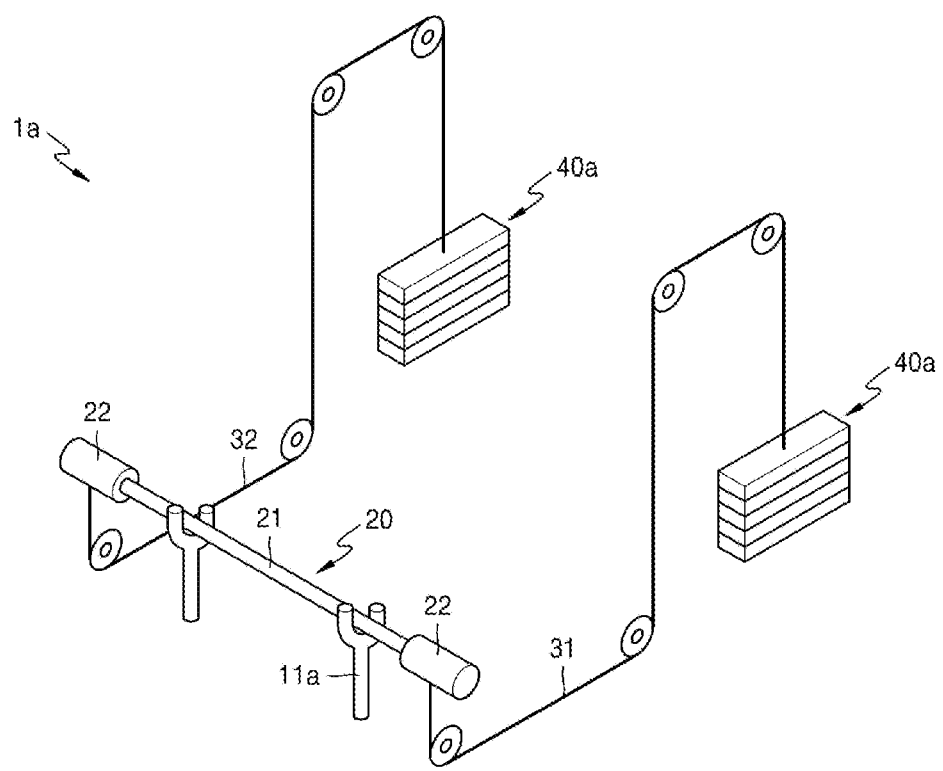
FIGS. 1 and 2 are conceptual views of a fitness structure adopting a double cable structure according to an embodiment.

As the inventive concept allows for various changes and numerous embodiments, embodiments will be illustrated in the drawings and described in detail in the written description. However, this is not intended to limit the present inventive concept to particular modes of practice, and it is to be appreciated that all changes, equivalents, and substitutes that do not depart from the spirit and technical scope of the present inventive concept are encompassed in the present inventive concept. In the description of the present inventive concept, certain detailed explanations of the related art are omitted when it is deemed that they may unnecessarily obscure the essence of the inventive concept. While such terms as "first," "second," etc., may be used to describe various components, such components must not be limited to the above terms. The above terms are used only to distinguish one component from another. An expression used in the singular encompasses the expression of the plural, unless it has a clearly different meaning in the context. In the present specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added. Sizes of components in the drawings may be exaggerated for convenience of explanation. In other words, since sizes and thicknesses of components in the drawings are arbitrarily illustrated for convenience of explanation, the following embodiments are not limited thereto.

Reference will now be made in detail to embodiments, examples of which are illustrated in the accompanying drawings. Like reference numerals in the drawings denote like elements, and thus their description will be omitted.

<Double Cable>

Figure 2:
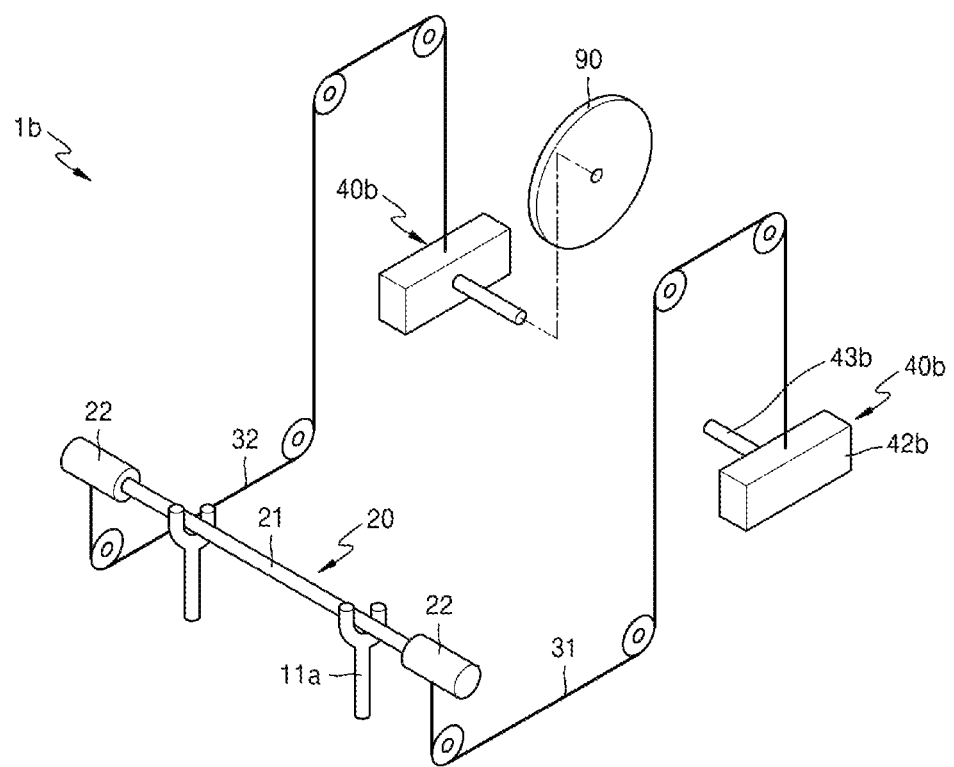

FIGS. 1 and 2 are conceptual views of a fitness structure adopting a double cable structure according to an embodiment.

In a general fitness structure according to the related art, since weight portions such as weight discs are placed at opposite ends of a bar, a large space is needed. For example, since a length of a bar of a general barbell is 220 cm, a necessary space may reach approximately 3 m when a space of about 30 cm for placing the weight portions at the opposite ends of a bar is taken into consideration. Furthermore, it is inconvenient for a user to move back and forth between the opposite ends of a fitness structure to change weight discs.

Although some fitness structures used by a cable connected to a weight portion have been developed, a pulley arranged to connect the cable to the weight portion closely contacts a rod and thus a safety accident may occur due to interference during exercise. Also, since a movement path of exercise in many cases frequently deviates vertically, a structure such as a frame of a fitness structure is spaced apart from the movement path of exercise.

To address the above problem, the fitness structure according to the present embodiment adopts a double cable structure. Referring to FIG. 1, in a fitness structure 1a according to the present embodiment, both of one end of a first cable 31 and one end of a second cable 32 are connected to opposite ends of the bar 20, and a load portion 40a is connected to both of the other end of the first cable 31 and the other end of the second cable 32, thereby enabling free weight exercise by using the two cables, namely, the first and second cables 31 and 32.

In detail, the fitness structure 1a according to the present embodiment may include the bar 20, the first cable 31, the second cable 32, and the two load portions 40a.

The bar 20 may include a bar main body 21 and a cable fixing portion 22 provided at opposite ends of the bar main body 21. The first cable 31 is connected to the cable fixing portion 22 formed at one end of the bar main body 21, whereas the second cable 32 is connected to the cable fixing portion 22 at the other end portion of the bar main body 21.

Although not illustrated, a bearing (not shown) is accommodated in at least one cable fixing portion 22, and thus, the bar main body 21 may be rotatable with respect to the cable fixing portion 22. Thus, the bearing may prevent damage to a wrist of the user during exercise.

One end of the first cable 31 is coupled to the cable fixing portion 22 of the bar 20, whereas the other end of the first cable 31 is coupled to the load portion 40a at one side. Also, one end of the second cable 32 is coupled to the cable fixing portion 22 of the bar 20, whereas the other end of the second cable 32 is coupled to the load portion 40a at the other side. In this state, one or more pulleys are arranged along each of the first and second cables 31 and 32 between the bar 20 and the load portion 40a. The pulleys transfer a force applied by the user to the load portion 40a while changing a direction of the force.

As illustrated in FIG. 1, the load portion 40a may have a stack structure. In this case, the weight of the load portion 40a may be adjusted by changing the position of a fixing pin (not shown). Although in the drawings the first and second cables 31 and 32, the load portion 40a, and a plurality of pulleys are combined to form a fixed pulley, the present disclosure is not limited thereto and various types such as a moving pulley or a compound pulley may be implemented according to an arrangement of cables, pulleys, and load portions.

Alternatively, as illustrated in FIG. 2, a load portion 40b may include an elevation portion 42b, where a weight coupling portion 43b is formed. As one or more weight portions 90 are coupled or decoupled with respect to the weight coupling portion 43b, the weight of the load portion 40b may be adjusted. In this state, the weight coupling portion 43b of the load portion 40b is placed inwardly in a fitness structure 1b so that the weight coupling portions 43b of the load portions 40b protrude in directions facing each other. Accordingly, an additional space for coupling the weight portions 90 outside the fitness structure 1b is unnecessary and thus there is an efficient space usage. In this case, various types such as a moving pulley or a compound pulley may be implemented according to an arrangement of cables, pulleys, and load portions.

A fitness structure having an improved efficiency of space usage may be implemented by using the double cable structure. In other words, although a barbell or smith machine needs a space of about 3 m to the left and right, the fitness structure 1a, 1b, or 1c according to the embodiments, in which a portion of the bar 20 held by the user during exercise is within 1.1 m from the center of the bar 20, may have an effect of reducing a width in a left and right direction of the fitness structure to about 1.5 m or less.

Also, the fitness structure 1a, 1b, or 1c according to the embodiments enables various exercises, in which the user is positioned between the bar 20 and the ground. In other words, the squat, the dead lift, the bench press, the barbell curl, the barbell row, the clean and jerk in weightlifting, or the snatch in weightlifting may be performed by using the fitness structure 1a, 1b, or 1c according to the embodiments. Also, since the fitness structure 1a, 1b, or 1c according to the embodiments has no separate guide portion, the bar 20 is not limited to a particular movement direction and thus free weight exercise, in which the bar 20 is freely moved in a direction in which the user applies a force, may be done. Accordingly, an effect of training balance muscles may be obtained.

Furthermore, in the fitness structure 1a, 1b, or 1c according to the embodiments, since no object such as a guide rod causing interference with the bar 20 during exercise is installed, a possibility that safety accidents may occur may be reduced.

Also, the user may adjust the weight standing at the middle of the bar 20 without having to move back and forth between the opposite ends of the bar 20 to adjust the weight. Accordingly, unnecessary movements of the user are reduced so that user convenience may be greatly improved.

A detailed embodiment adopting the double cable structure is described below in detail with reference to FIG. 6.

<Air Loading>

Figure 3:
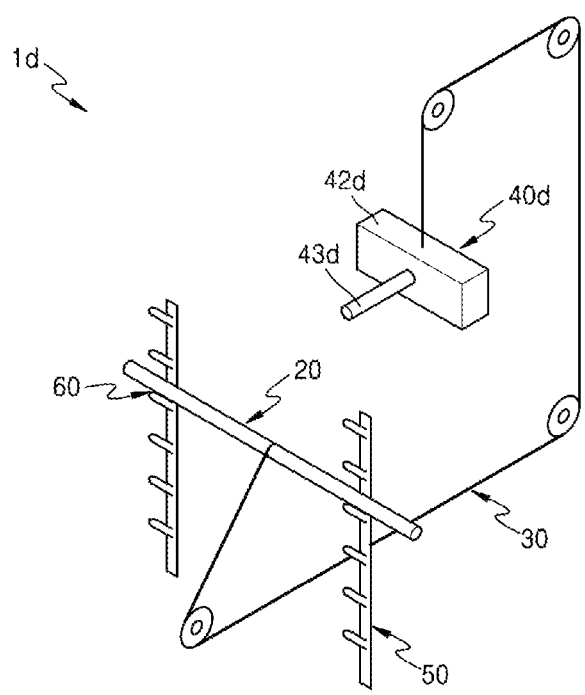
FIGS. 3, 4, and 5 are conceptual views of a fitness structure adopting an air loading structure according to an embodiment.
Figure 4:
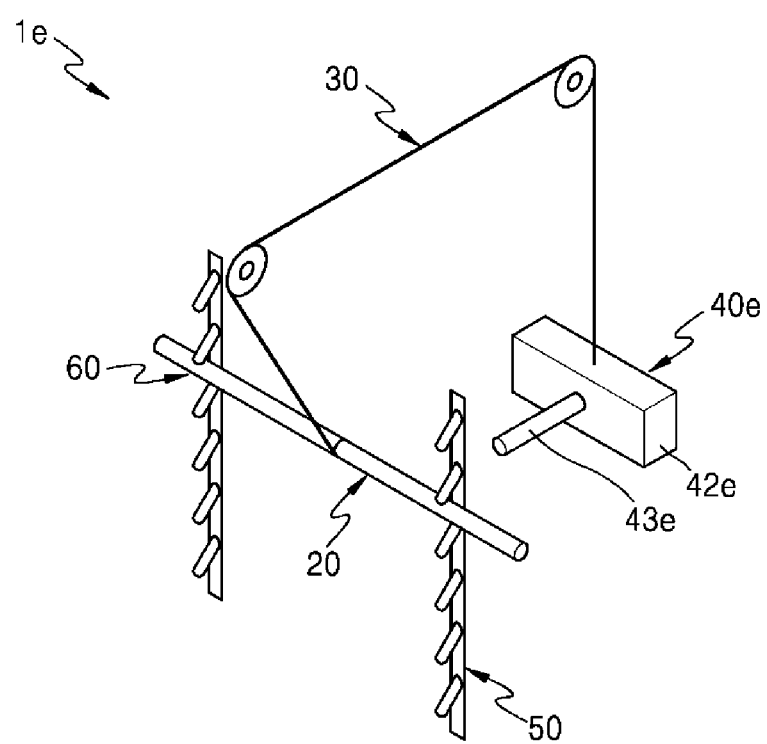
Figure 5:
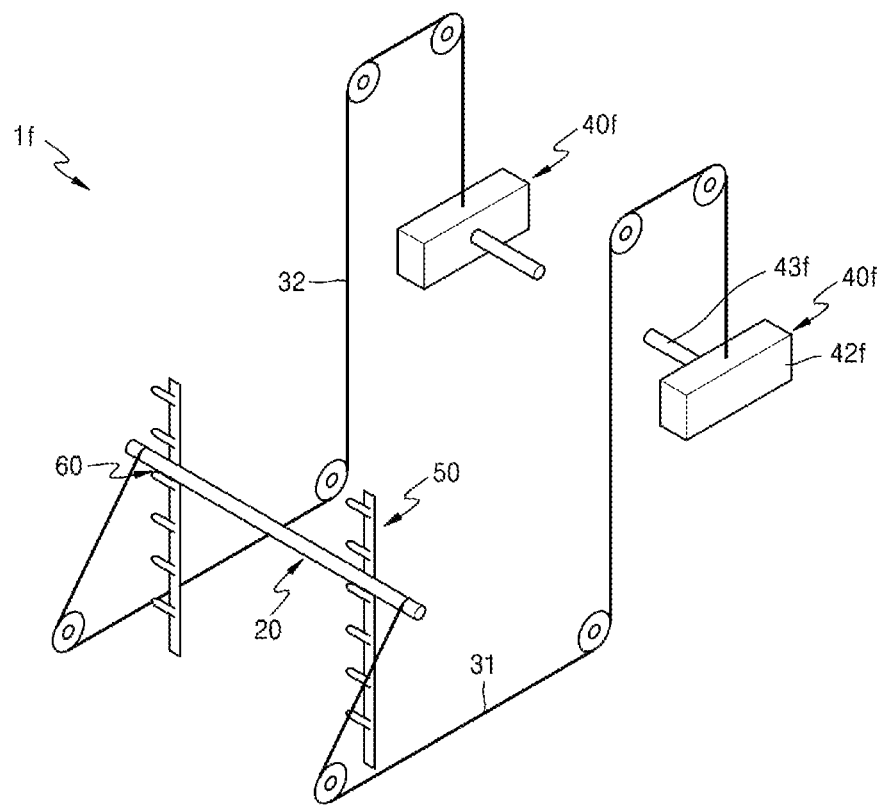

FIGS. 3, 4, and 5 are conceptual views of a fitness structure adopting an air loading structure according to an embodiment.

In the case of a general fitness structure according to a related art, it is a problem that the general fitness structure does not correspond to various exercise start positions. In detail, although the position of a bar or handle where a user starts to exercise varies depending on a type of exercise or a body type of the user, a start position of a weight machine according to a related art is fixed. For example, for a lat pull down exercise, when a tall user sets a handle to match his/her height, a relatively short user is not able to grab the handle. Also, in equipment in which a force of weight transferred via a cable acts in the direction of gravity, the position of a bar is fixed and thus the equipment may not correspond to various exercises.

Although adjustable pulleys to change the position of a bar have been developed, there are still many exercises that cannot be performed due to a limit in a block structure.

In detail, when stretched, muscle characteristically returns to the original state thereof like a rubber string. These characteristics are referred to as stretch reflex. When one stretches oneself and then relaxes, the body returns to the original state thereof due to the stretch reflex of the chest muscle (pectoralis major).

Weight training includes exercises using stretch reflex and exercises not using stretch reflex. The Romanian dead lift and squat are exercises using the stretch reflex of the hamstring; the bench press is an exercise using the stretch reflex of the chest; and the cable triceps pushdown is an exercise using stretch reflex of the triceps. In contrast, the barbell curl, the dead lift, and chin-ups are exercises that do not use stretch reflex, in which the exercise starts from a state of not applying a force to the bar, that is, in a stable state.

For convenience of explanation, an exercise using the stretch reflex of lowering and lifting up a weight in a state of the weight already lifted up, that is, a state in which a force is applied to the weight, may be referred to as a downward exercise. In contrast, an exercise of lifting up a weight from a stable state of relaxing the weight, that is, a state in which the weight lowered to a relaxed position may be referred to as an upward exercise.

The reasons for using stretch reflex are that heavier weight may be lifted, compared to a case of lifting the weight without using stretch reflex, and that an effect of training is high because the exercise using stretch reflex is similar to motions of a body in actual daily life. The squat is a downward exercise of lowering and raising the weight, starting from a state of lifting the weight. If the exercise of lifting the weight starts from a state of sitting, which is called box squat because the user starts to exercise sitting on a box, that is, the exercise is an upward exercise, the user may lift only a quite light weight.

In a method in which a loading member penetrates through a plurality of blocks previously stacked and a weight to use is selected by using a weight pin, like adjustable pulleys, while the upward exercise is possible, the downward exercise is not possible. This is because, for the downward exercise such as a squat, a weight block being used during exercise should not contact a stacked block and thus it is difficult to lift the weight from a position lower than the lowest position of an exercise path, that is, a position where the block is placed, toward the highest position of the exercise path, when taking an exercise start pose. In particular, for an exercise using a heavy weight that is heavier than one's weight, like squat, it is difficult to take an exercise start pose.

Also, for the adjustable pulley, since a guide rod for moving the position of a handle causes interference during exercise, there is a possibility of a safety accident and thus various exercise motions may not be performed.

In the exercise equipment using blocks and cables according to a related art, noise and vibrations are generated when the block is placed at the original position and unused blocks are placed altogether so that assembly and movement are difficult and unnecessary costs are generated. Also, although the smith machine has been developed to correspond to various exercise start positions, since the exercise path cannot be deviated from a guide rail, it is difficult to expect an effect of free weight exercise for improving balanced muscles.

In order to address the above problem, a fitness structure according to the present embodiment adopts an "Air Loading" structure so that a weight portion (not shown) may be detachably provided regardless of the position of the bar 20.

Referring to FIG. 3, a fitness structure 1d according to the present embodiment may include the bar 20, a cable 30, a load portion 40d, a bar support portion 50, and a bar support member 60. In this state, the bar support portion 50 has a standing structure and one or more bar support members 60 coupled to the bar support portion 50 are provided so that the bar 20 may be placed at various heights. Also, the load portion 40d is connected to the bar 20 via the cable 30 such that the position or height of the load portion 40d is changed corresponding to the position of the bar 20. The load portion 40d may include an elevation portion 42d having a weight coupling portion 43d. One or more weight portions (not shown) are coupled to the weight coupling portion 43d so that the weight of the load portion 40d may be adjusted. As such, as the load portion 40d, of which the position or height is changed corresponding to the position of the bar 20, is provided, the weight portions may be detachably provided regardless of the position of the bar 20 (not shown).

In the fitness structure 1d according to the present embodiment, even when the bar 20 is lowered as lowest as possible, the load portion 40d may be spaced apart from the fitness structure 1d without contacting the same. Also, for the bar support portion 50, the standing structure may be located perpendicular to the ground or inclined by a certain angle with respect to a direction perpendicular to the ground.

As illustrated in FIG. 3, the cable 30 connecting the bar 20 to the load portion 40d may be connected in a downward direction from the bar 20. Alternatively, as illustrated in FIG. 4, the cable 30 connecting the bar 20 to a load portion 40e may be connected in an upward direction from the bar 20. In other words, the bar 20, to which the cable 30 is connected, may be placed at various positions regardless of the direction of the cable 30. Furthermore, even when the position of the load portion 40d and 40e is changed according to the position of the bar 20, a weight may be added or subtracted regardless of the above change.

Also, as illustrated in FIG. 5, two or more first and second cables 31 and 32 are provided such that both of one end of the first cable 31 and one end of the second cable 32 are connected to the opposite ends of the bar 20 and the load portion 40f is connected to both of the other end of the first cable 31 and the other end of the second cable 32. Accordingly, free weight exercise may be performed by using the two first and second cables 31 and 32. In this state, each load portion 40f may include an elevation portion 42f, where a weight coupling portion 43f is formed. One or more weight portions (not shown) are coupled to the weight coupling portion 43f to adjust the weight of the load portion 40f. The weight coupling portion 43f of each load portion 40f is placed inwardly in the fitness structure 1f and thus the weight coupling portions 43f of the two load portions 40f may protrude in directions facing each other.

Although FIG. 5 illustrates that the first and second cables 31 and 32, the load portion 40f, and a plurality of pulleys are combined forming a fixed pulley, the present disclosure is not limited thereto, various types such as a moving pulley or a compound pulley may be implemented according to an arrangement of cables, pulleys, and load portions.

As such, as the air loading structure is adopted, the weight may be adjusted at various heights corresponding to exercises having different start positions. Also, the fitness structure may be used by setting a start position to be a height appropriate for a body type of each user. Accordingly, various exercises such as the barbell curl, the Romanian dead lift, the dead lift, and the barbell row are available. Furthermore, since a pulley for changing a load in a horizontal direction with respect to the ground to a vertical direction is independently provided, exercise may be performed without interference.

Also, since the fitness structures 1d, 1e, and 1f according to the present embodiments have no separate guide portion unlike a smith machine according to the related art, the bar 20 is not limited to a particular movement direction and thus free weight exercise, in which the bar 20 is freely moved in a direction in which the user applies a force, may be done. Accordingly, an effect of training balanced muscles may be obtained.

Furthermore, since the fitness structures 1d, 1e, and 1f according to the present embodiments do not use weight blocks, installation, assembly, and movement of the fitness structure are easy. For a fitness club, since weight discs may be used, raw costs may be reduced. Also, since weight blocks do not bump each other when the bar is placed in position after exercise is completed, noise and vibrations may be reduced.

A detailed embodiment adopting the air loading structure is described below in detail with reference to FIG. 6.

Embodiment

Figure 6:
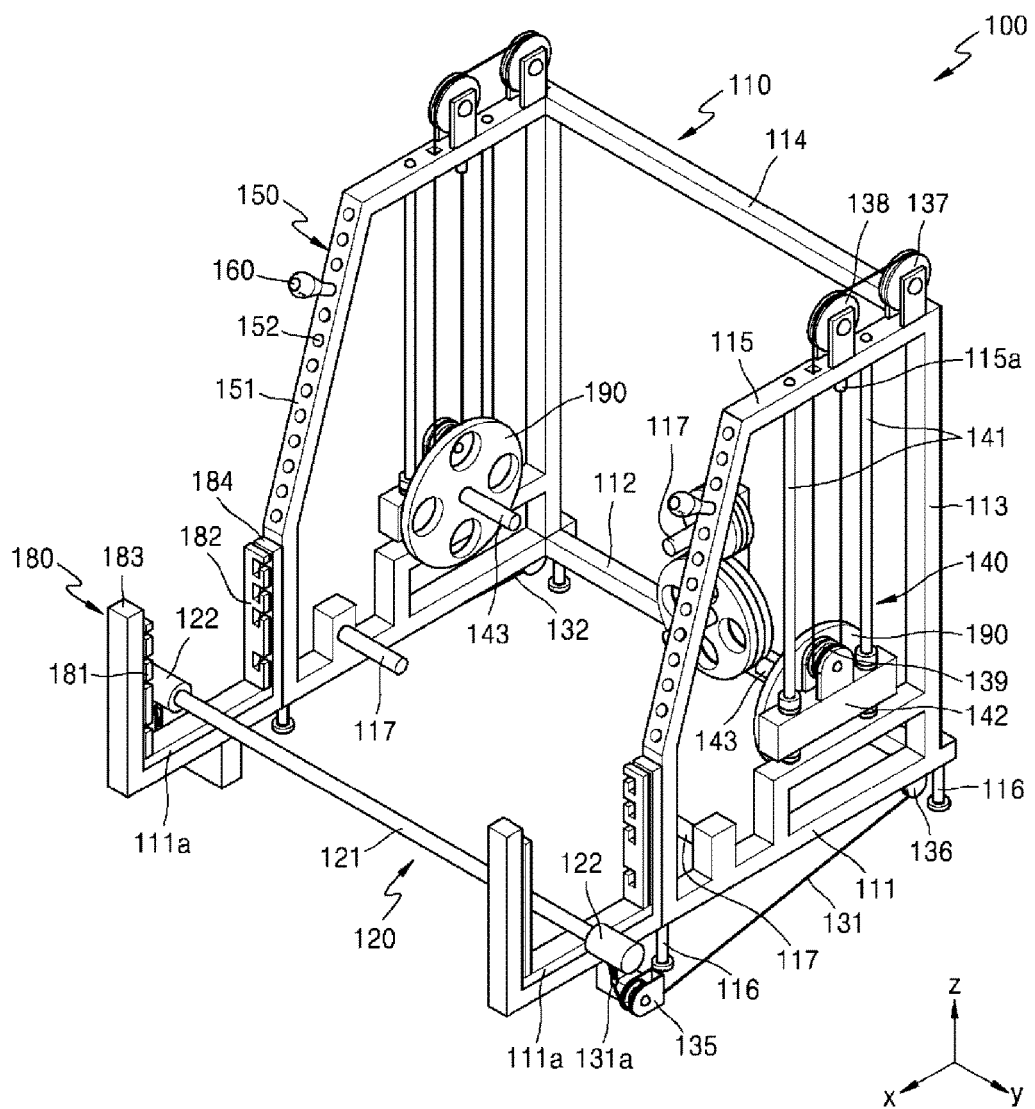
FIG. 6 is a perspective view of a fitness structure according to an embodiment.
Figure 7:
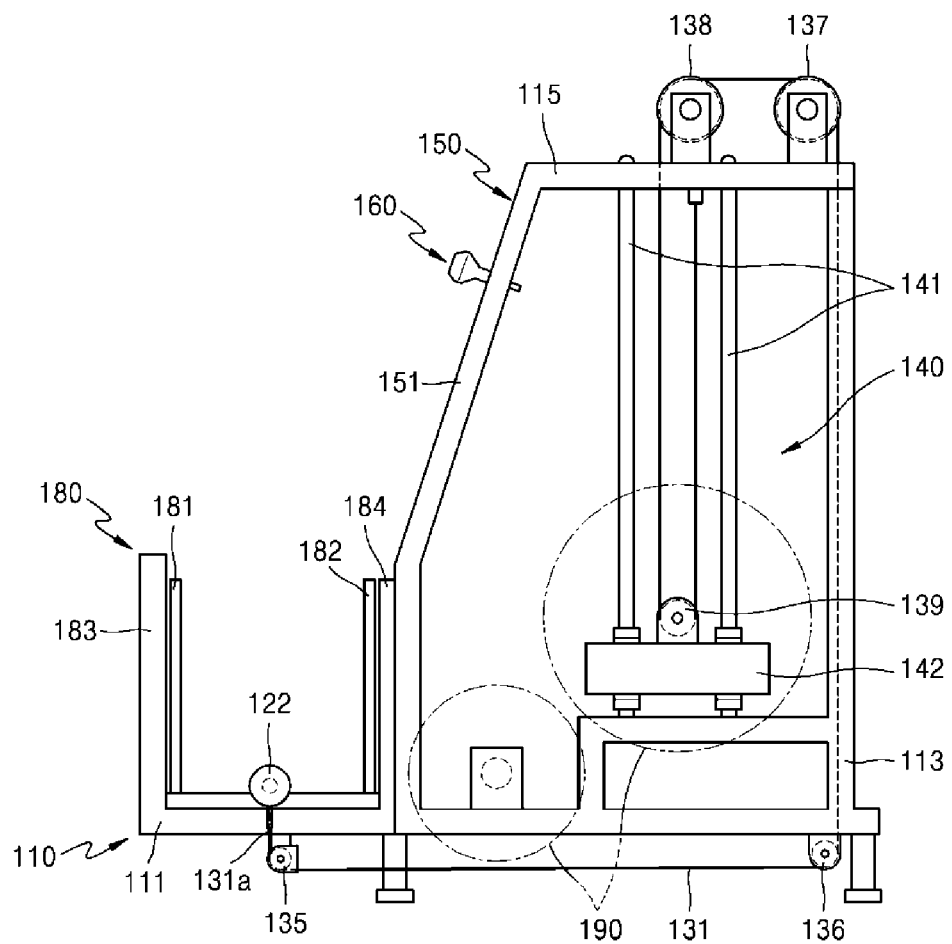
FIG. 7 is a side view of the fitness structure of FIG. 6.
Figure 8:
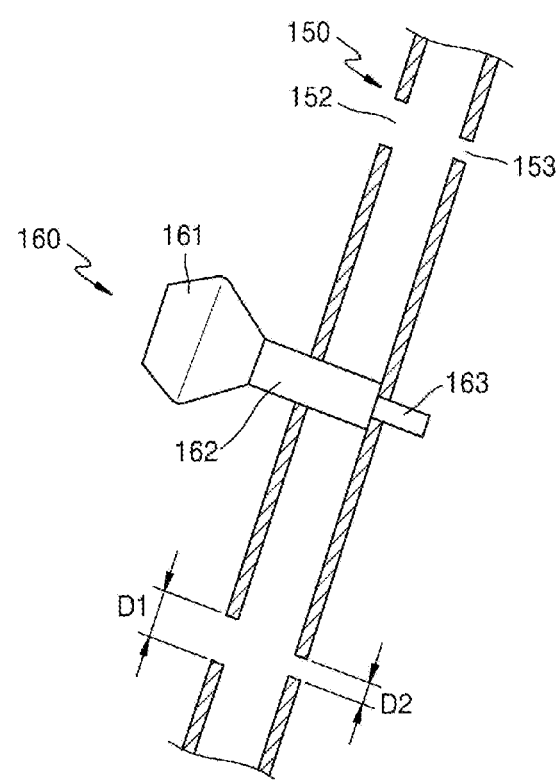
FIG. 8 is a side view of a bar support portion and a bar support member of the fitness structure of FIG. 6.
Figure 9:
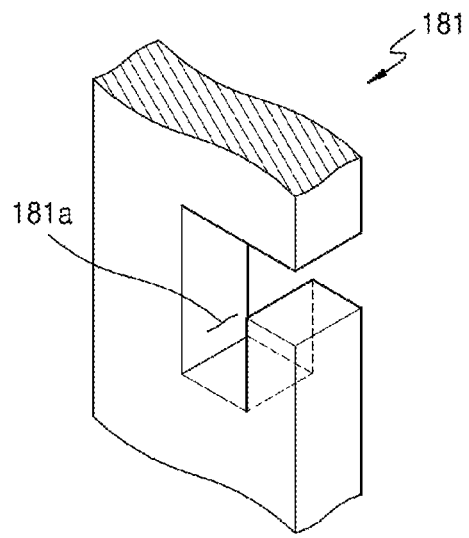
FIG. 9 is a perspective view of a first standing member of a catcher bar support portion of the fitness structure of FIG. 6.
Figure 10:
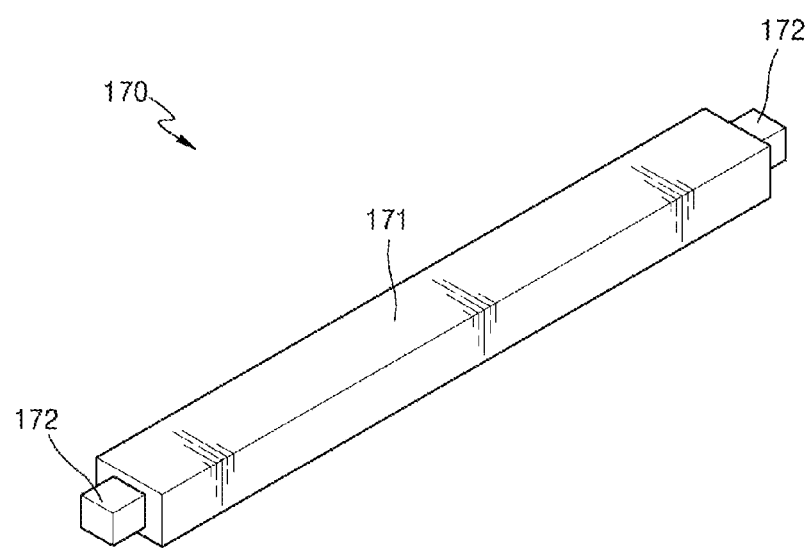
FIG. 10 is a perspective view of the catcher bar of the fitness structure of FIG. 6.
Figure 11:
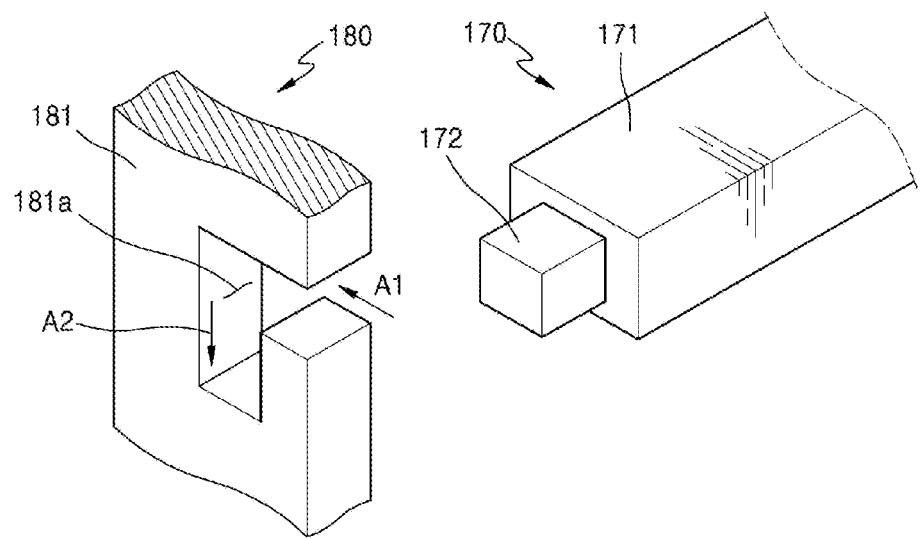
FIGS. 11 and 12 are perspective views illustrating a state in which the catcher bar of FIG. 6 is coupled to the first standing member.
Figure 12:
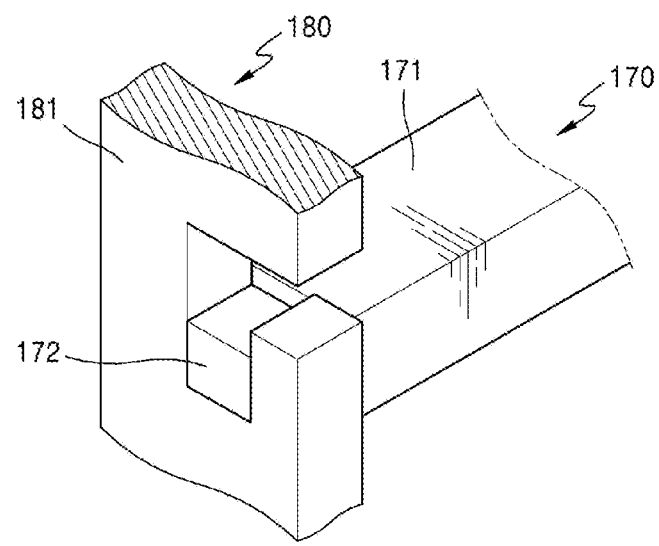

FIG. 6 is a perspective view of a fitness structure according to an embodiment. FIG. 7 is a side view of the fitness structure of FIG. 6. FIG. 8 is a side view of a bar support portion and a bar support member of the fitness structure of FIG. 6. FIG. 9 is a perspective view of a first standing member of a catcher bar support portion of the fitness structure of FIG. 6. FIG. 10 is a perspective view of the catcher bar of the fitness structure of FIG. 6. FIGS. 11 and 12 are perspective views illustrating a state in which the catcher bar of FIG. 6 is coupled to the first standing member.

First, referring to FIGS. 6 and 7, a fitness structure 100 according to an embodiment may include a frame 110, a bar 120, a first cable 131, a second cable 132, a load portion 140, a bar support portion 150, a bar support member 160, a catcher bar 170, a catcher bar support portion 180, and a weight portion 190, which are described below in detail.

The frame 110 forms a base portion of the fitness structure 100, where constituent elements to be described later are formed, and supports the constituent elements. Each part of the frame 110 may be formed of a material having rigidity, for example, iron (Fe) or an iron alloy.

The frame 110 may include a pair of first frames 111 extending in a first direction (X-axis direction), a second frame 112 extending in a second direction (Y-axis direction) and connecting the pair of first frames 111, a pair of third frames 113 extending in a third direction (Z-axis direction) from a connection portion between the first frames 111 and the second frame 112. Furthermore, the frame 110 may further include a fourth frame 114 extending in the second direction (Y-axis direction) and connecting the pair of third frames 113, and a pair of fifth frames 115 extending in the first direction (X-axis direction) from a connection portion between each of the third frames 113 and the fourth frame 114. Although in the drawings each of the first to fifth frames 111~115 is illustrated to have a rectangular column shape, the present disclosure is not limited thereto, and the first to fifth frames 111~115 may have various shapes, lengths, and materials to form the frame 110 of the fitness structure 100, for example, a circular column or a polygonal column. Also, although in the drawings the first to fifth frames 111~115 are illustrated to be formed in perpendicular directions to one another, the present disclosure is not limited thereto, and the first to fifth frames 111~115 may be formed in various ways to have a certain angle, not to be perpendicular, with respect to one another according to the structure of the fitness structure 100.

A bar accommodation portion 111a, where the bar 120 is accommodated, may be formed on one end of each of the first frames 111. The bar accommodation portion 111a may be formed integrally with each of the first frames 111 or by coupling a separate member to one end of each of the first frames 111.

The frame 110 may further include a plurality of leg portions 116. The leg portions 116 may allow the frame 110 to be largely spaced apart from the ground to a degree, and a position, length, and shape of the leg portions 116 may be variously changed, as necessary.

The frame 110 may further include one or more weight support portions 117. Each of the weight support portions 117 may protrude inwardly in the fitness structure 100. Accordingly, a separate space for coupling the weight portion 190 outside the fitness structure 100 is unnecessary and thus there is an efficient space usage.

The bar 120 may include a bar main body 121 and a cable fixing portion 122 on each of opposite end portions of the bar main body 121. The first cable 131 may be connected to the cable fixing portion 122 on one end portion of the bar main body 121, and the second cable 132 may be connected to the cable fixing portion 122 on the other end portion of the bar main body 121.

A user may move the bar 120 by applying a force over the weight of the load portion 140 while holding the bar 120 in an exercise pose. A movement direction of the bar 120 is not limited to a particular movement direction and the bar 120 may be freely moved in a direction in which the user's force is applied. In other words, the user may perform free weight exercise by using the bar 120.

Although not illustrated, a bearing (not shown) is accommodated in at least one cable fixing portion 122 so that the bar main body 121 may be rotatable with respect to the cable fixing portion 122. During exercise, a wrist of the user may not be hurt due to the bearing.

One end of the first cable 131 may be coupled to the cable fixing portion 122 on the one end portion of the bar 120, whereas the other end of the first cable 131 may be coupled to a fixing portion 115a of the fifth frame 115 via the load portion 140 at one side. Also, one end of the second cable 132 may be coupled to the cable fixing portion 122 on the other end portion of the bar 120, whereas the other end of the second cable 132 may be coupled to the fixing portion 115a of the fifth frame 115 via the load portion 140 at the other side. A connection member 131a of a ring type may be further formed at the one end of the first cable 131 to connect the first cable 131 to the bar 120. Likewise, a connection member (not shown) of a ring type may be further formed at the one end of the second cable 132 to connect the second cable 132 to the bar 120.

One or more pulleys 135, 136, 137, 138, and 139 are arranged in the middle of each of the first and second cables 131 and 132 connecting the bar 120 to the load portion 140. The pulleys 135, 136, 137, 138, and 139 change directions of a force applied by the user to the bar 120 while delivering the force to the load portion 140. Although in the drawings the first and second cables 131 and 132, the load portion 140, and the pulleys 135, 136, 137, 138, and 139 are illustrated to be coupled to one another forming a fixed pulley, the present disclosure is not limited thereto, various types such as a moving pulley or a compound pulley may be implemented according to an arrangement of cables, pulleys, and load portions.

The load portion 140 may enable combining of the weight portions 190 and provides a load opposing a force applied by the user when using the fitness structure 100. The load portion 140 has a structure to generate a force opposing the weight of the user and is not limited to a particular structure. For example, the weight may be adjusted as the user selects one of a plurality of blocks. Also, a strength of an elastic force may be adjusted by using a coil spring having a variable elasticity or as the user selects one of rubber bands having different elastic coefficients. Furthermore, a load apparatus of various types using oil pressure or air pressure may be included as the load portion 140. However, in the following description, for convenience of explanation, a case in which the load portion 140 may adjust the weight by combining a plurality of the weight portions 190 having a disc shape is mainly described.

The load portion 140 arranged in a pair to face each other may include a guide portion 141, an elevation portion 142, and a weight coupling portion 143. The guide portion 141 is provided as one or more rods extending in the third direction (Z-axis direction), thereby guiding an elevation movement of the elevation portion 142 in the third direction (Z-axis direction). The elevation portion 142 has a certain block shape and may elevate along the guide portion 141 in the third direction (Z-axis direction). The weight coupling portion 143 protrudes from the elevation portion 142 in one direction to detachably combine one or more of the weight portions 190. In other words, as one or more of the weight portions 190 are detachably combined to the weight coupling portion 143, the weight of the load portion 140 may be adjusted. The weight coupling portion 143 of each load portion 140 is placed inwardly in the fitness structure 100, that is, the weight coupling portions 143 of the two load portions 140 may protrude in directions facing each other.

Accordingly, since a separate space for combining the weight portion 190 is unnecessary outside the fitness structure 100, a more efficient space usage may be available.

Referring to FIGS. 6, 7, and 8, the bar support portion 150 and the bar support member 160 may facilitate that the bar 120 is placed at various heights.

In detail, the bar support portion 150 may include a support frame 151 having hollow frame shape. A first insertion hole 152 may be formed in one surface (upper surface) of the support frame 151, whereas a second insertion hole 153 may be formed in the other surface (lower surface) of the support frame 151. An upper portion of the support frame 151 may be formed to be inclined by a certain degree from the third direction (Z-axis direction), whereas a lower portion of the support frame 151 may be formed approximately in the third direction (Z-axis direction). In other words, an upper frame of the support frame 151 may be connected to a lower frame that is perpendicular to the ground by being inclined by a certain degree. Accordingly, the upper frame may be arranged to be inclined by a certain degree with respect to a direction perpendicular to the ground.

The first insertion hole 152 formed in the upper surface of the support frame 151 of the bar support portion 150 may have a first diameter D1, whereas the second insertion hole 153 formed in the lower surface of the support frame 151 may have a second diameter D2. In this state, the first insertion hole 152 and the second insertion hole 153 at least partially overlap each other so that the bar support member 160 may be inserted through the first insertion hole 152 and the second insertion hole 153.

The bar support member 160, which is coupled to the support frame 151, may include a head portion 161, a first diametric portion 162, and a second diametric portion 163. The head portion 161 may have a roughly conic shape. Accordingly, the bar support member 160 may prevent the bar 120 placed on the bar support portion 150 from falling therefrom. The first diametric portion 162 is at one side of the head portion 161, and the second diametric portion 163 is formed at one side of the first diametric portion 162. In this state, the diameter of the first diametric portion 162 may be equal to or slightly less than the first diameter D1 of the first insertion hole 152, whereas the diameter of the second diametric portion 163 may be equal to or slightly less than the second diameter D2 of the second insertion hole 153.

The bar support member 160 may be inserted in any one of the first insertion holes 152 and the second insertion holes 153 corresponding to the first insertion holes 152, in the support frame 151. The bar support member 160 is located at each of the bar support portions 150 at the same height.

When the bar support member 160 is inserted in the bar support portion 150, the second diametric portion 163 penetrates through the second insertion hole 153 in a direction from a front side to a rear side. In this case, since the diameter of the first diametric portion 162 is greater than the second diameter D2 of the second insertion hole 153, the first diametric portion 162 does not penetrate through the second insertion hole 153 and may support the bar support member 160. Also, the head portion 161 protrudes from the upper surface of the support frame 151 to a degree and thus the bar 120 may be stably placed between the head portion 161 and the support frame 151. The shape of the first insertion hole 152 and the shape of a section of the first diametric portion 162, or the shape of the second insertion hole 153 and the shape of a section of the second diametric portion 163, may be a figure similar to each other, and the figure may be any one of a polygon and a circle.

Referring to FIGS. 6 and 7 and FIGS. 9 to 13, the catcher bar support portion 180 may stably support the catcher bar 170.

The catcher bar 170 may prevent the user from getting hurt by supporting the bar 120 at a certain height in a situation where the user loses a control over the bar 120, for example, the bar 120 slips out of the user's hands during a weight training motion or the user tumbles backward while lifting up the bar 120. Also, according to a type of usage pattern of the user, the catcher bar 170 may be used to support the bar 120 on an upper surface thereof.

The catcher bar 170 may include a bar support part 171 extending in one direction and a pair of insertion/detachment parts 172 at opposite end portions of the bar support part 171. An upper surface of the bar support part 171 may be formed to be substantially flat to increase a frictional area with respect to the bar 120. Although not illustrated, a rubber pad may be attached on the upper surface of the bar support part 171. The catcher bar 170 may be provided as the insertion/detachment parts 172 are inserted into guide holes of a first standing member 181 and a second standing member 182.

The catcher bar support portion 180 may include the first standing member 181 and the second standing member 182 facing each other. Furthermore, the catcher bar support portion 180 may further include a first support member 183 at one side of the first standing member 181 and a second guide member 184 at one side of the second standing member 182.

The first standing member 181 may include a plurality of first guiding grooves 181a at different heights, whereas the second standing member 182 may include a plurality of guiding grooves respectively corresponding to the first guiding grooves 181a. The guiding grooves of the second standing member 182 may have substantially the same shape as the first guiding grooves 181a of the first standing member 181. The guiding grooves of the second standing member 182 may be formed at substantially the same heights of the first guiding grooves 181a of the first standing member 181 corresponding thereto. FIG. 6 illustrates that each of the first and second standing members 181 and 182 includes four guiding grooves having different heights. However, this is merely exemplary and the number of guiding grooves included in the first and second standing members 181 and 182 may be variously set as necessary.

The first standing member 181 may include the first guiding grooves 181a, each being indented into a certain inner space. Each of the first guiding grooves 181a has an open portion, a horizontal groove connected to the open portion, and a vertical groove connected to the horizontal groove. An accommodation portion is located in a lower end of the vertical groove and the accommodation portion may have a substantially flat surface. In other words, each of the first guiding grooves 181a may have a "]" shape including the horizontal groove and the vertical groove.

Referring to FIGS. 11 and 12, the catcher bar 170 is provided on the first standing member 181 as the insertion/detachment parts 172 are inserted through the open portion of the first guiding grooves 181a horizontally along an arrow A1 and then vertically along an arrow A2, to be accommodated on a bottom surface of one of the first guiding grooves 181a.

As such, according to the present embodiment, the catcher bar support portion 180 of the fitness structure 100 includes the first guiding grooves 181a having a "]" shape, and the catcher bar 170 inserted into one of the first guiding grooves 181a includes the insertion/detachment parts 172 having a rectangular vertical section. As such, since the catcher bar 170 is stably fixed on the catcher bar support portion 180 due to the structures of the catcher bar 170 and the catcher bar support portion 180, the bar 120 may be further stably supported.

Also, since each of the first and second standing members 181 and 182 includes the first guiding grooves 181*a* having different heights, even when a plurality of users use the same fitness structure, the catcher bar 170 may be easily placed at an appropriate height according to a body type of each user.

Figure 13:
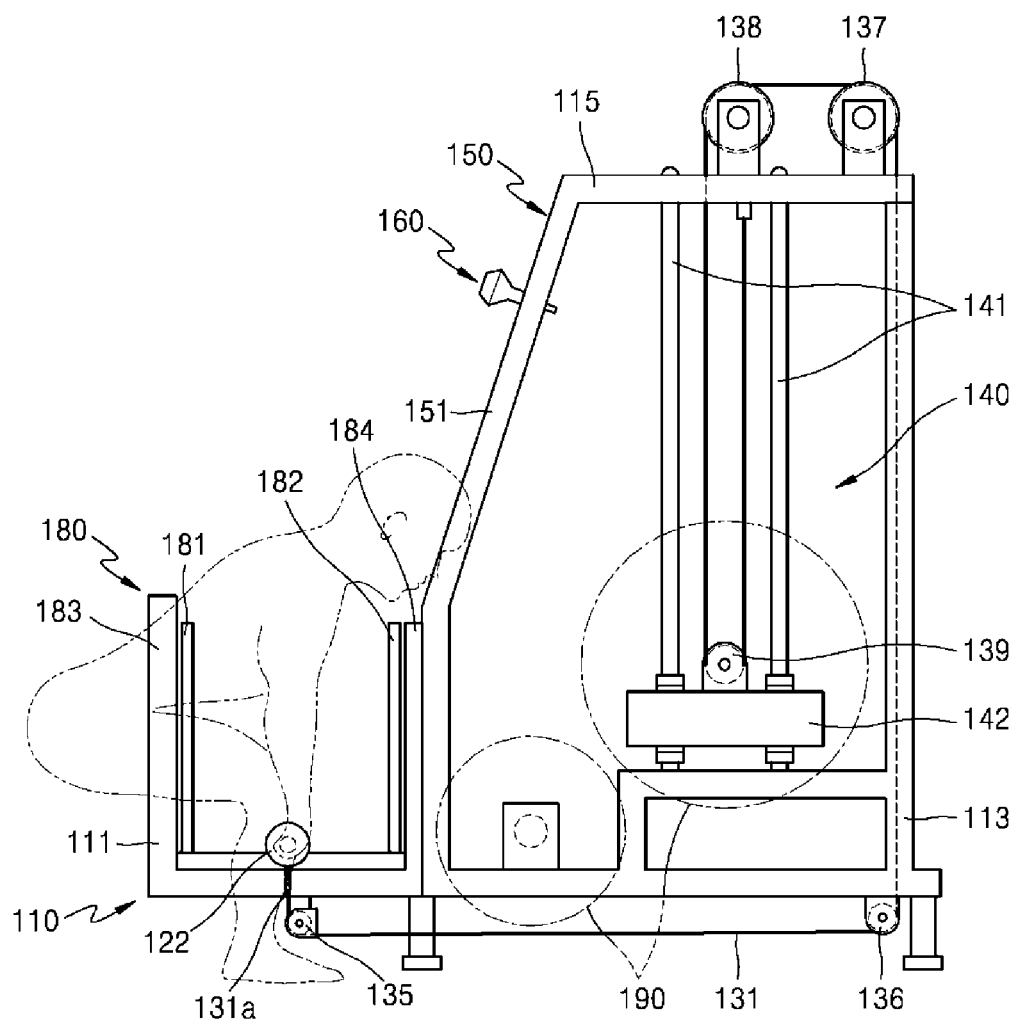
FIG. 13 is a side view illustrating a user performing a dead lift by using the fitness structure of FIG. 6.

FIG. 13 is a side view illustrating a user performing a dead lift by using the fitness structure according to the embodiment. Referring to FIG. 13, according to the fitness structure according to the present embodiment, free weight exercise, in which the bar 120 may freely move along a direction of a force applied by the user, without being limited to a particular movement direction, is possible. Accordingly, an effect of training balanced muscles may be obtained.

Figure 14:
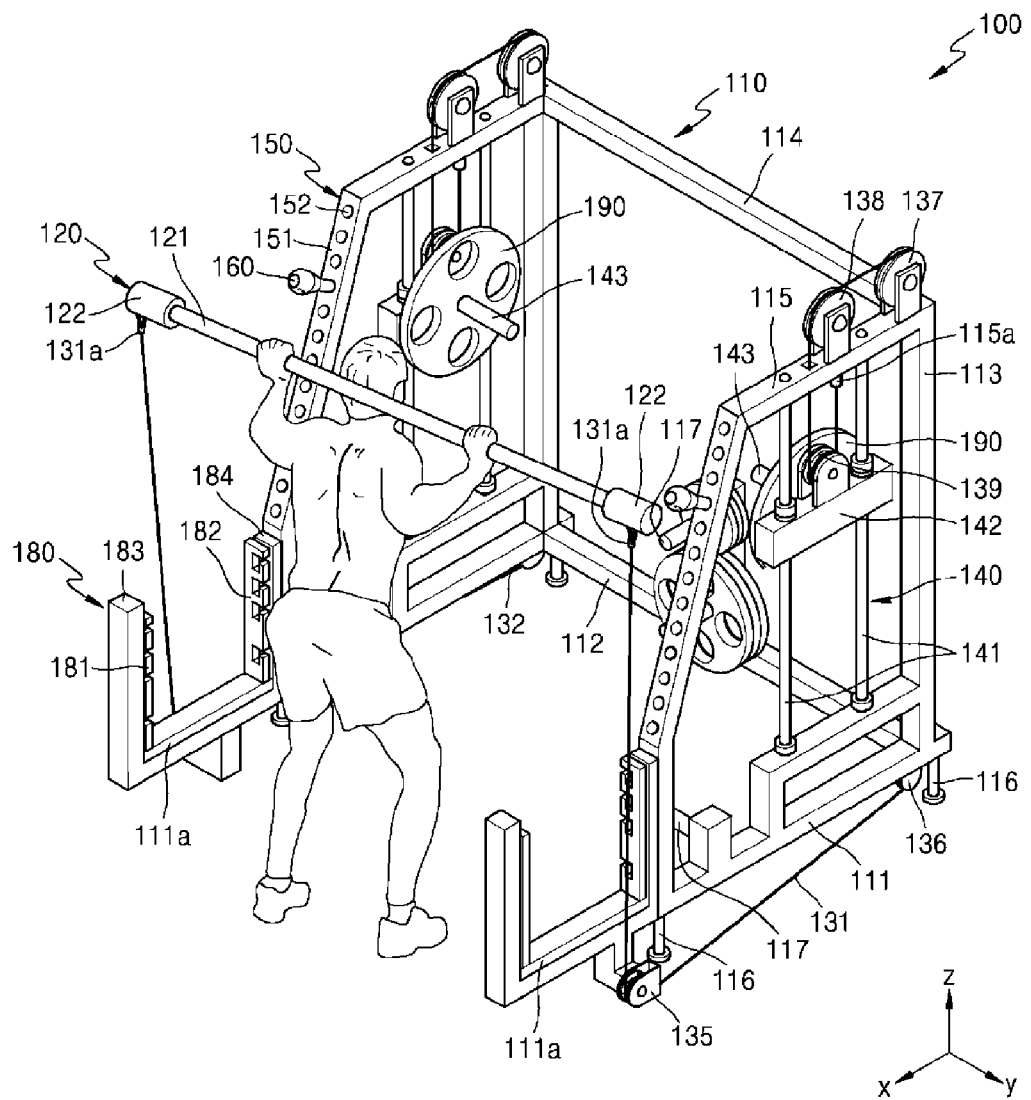
FIG. 14 is a perspective view illustrating a user performing a squat by using the fitness structure of FIG. 6.

FIG. 14 is a perspective view illustrating a user performing a squat by using the fitness structure according to the embodiment. Referring to FIG. 14, according to the fitness structure according to the embodiment, since the insertion pin is inserted into the insertion hole located at an appropriate height in the standing structure including the insertion holes, even when a plurality of users uses the same fitness structure, the bar 120 may be easily placed according to the height of each user.

Although not illustrated, the load portion 140 may be further provided with a distance sensor (not shown) for measuring a movement distance of the load portion 140. Since the movement distance, direction, and speed of the load portion 140 are measured by the distance sensor, an amount of exercise of a user may be automatically measured.

In the following description, an exercise management system 2 using the fitness structure 100 according to an embodiment is described.

Figure 15:
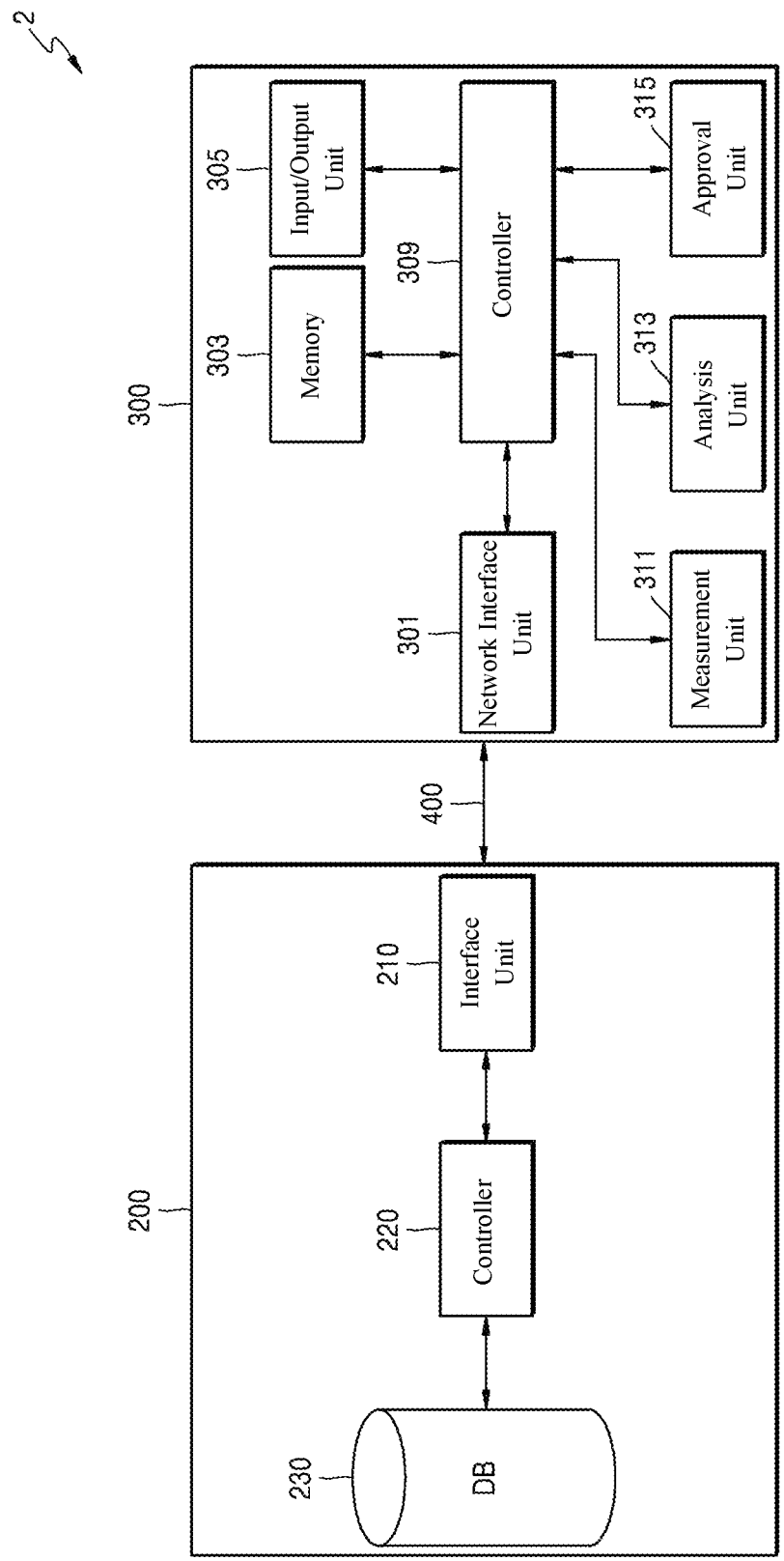
FIG. 15 is a block diagram of an exercise management system using the fitness structure of FIG. 6.

FIG. 15 is a block diagram of the exercise management system 2 using the fitness structure 100 of FIG. 6. Referring to FIG. 15, the exercise management system 2 using the fitness structure 100 according to the present embodiment may include an exercise management server 200 and an exercise analysis apparatus 300. Also, the exercise management system 2 may include a communication network 400 connecting a plurality of the exercise analysis apparatuses 300 and the exercise management server 200.

The exercise management server 200 may include an interface unit 210, a controller 220, and a database 230.

In detail, the interface unit 210 provides a communication interface for supplying transmitting/receiving signals between the exercise management server 200 and the exercise analysis apparatus 300, as packet data, interlinked with the communication network 400.

The controller 220 analyzes exercise data of each user received from the exercise analysis apparatus 300 via the interface unit 210, and transmits a result of the analysis to the exercise analysis apparatus 300 via the interface unit 210.

The database 230 may store the exercise data of each user received from the exercise analysis apparatus 300 and the analysis result thereof. Furthermore, the database 230 may further include a user database for storing user information. The user database stores user information about users who use the exercise management system 2. The user information may include basic information about a user such as the name, position, personal data, gender, age, etc., information about a login such as the identity (ID) and password (PW), information about access country, access location, and an apparatus used for access, and information related to a network environment for access.

Also, although not illustrated, according to the present embodiment, the exercise management server 200 may further include a memory, an input/output unit, and a program storing unit.

The exercise analysis apparatus 300 may include a network interface unit 301, a memory 303, an input/output unit 305, a controller 309, a measurement unit 311, an analysis unit 313, and a user approval unit 315.

In detail, the network interface unit 301 provides a communication interface for transmitting exercise data and receiving a result of the analysis, interlinked with the communication network 400.

The memory 303 temporarily stores data processed by the controller 309 or temporarily stores exercise data measured or analyzed by the exercise analysis apparatus 300.

The input/output unit 305 may include a touch recognition display controller and other input/output controllers. The touch recognition display controller provides an output interface and an input interface between an apparatus and a user. The touch recognition display controller transmits/receives electric signals with respect to the controller 309. Also, the touch recognition display controller may display a visual output to the user, and the visual output may include text, graphics, images, videos, and a combination thereof. The other input/output controller may control an input and an output of other peripheral devices such as a power unit, a speaker unit, or a microphone. The input/output unit 305 may be a certain display member, for example, an organic light emitting display (OLED) or a liquid crystal display (LCD) capable of performing touch recognition.

The controller 309 is a sort of a central processing unit and controls an overall process of providing an exercise analysis service in the exercise analysis apparatus 300. In other words, the controller 309 provides various services such as driving software on a program storing unit (not shown), extracting a measured value from each sensor included the measurement unit 311 by controlling the measurement unit 311, analyzing a type of exercise, a frequency of exercise, or an exercise weight from the measured value extracted by the measurement unit 311 by controlling the analysis unit 313, approving a user currently using the fitness structure 100 of FIG. 6 by controlling the user approval unit 315, and providing a result of the analysis by the analysis unit 313 to each user.

The measurement unit 311 extracts a measured value from each sensor included in the measurement unit 311 by the control of the controller 309. The measurement unit 311 may include a sensor for sensing the weight of a weight portion, a sensor for sensing the position of a weight portion or a user's body, a sensor for sensing acceleration of a weight portion or the user's body, a sensor for sensing an exercise time, and a sensor for sensing a movement distance of a weight portion or the user's body. In addition to the above sensors, any sensor may be included even when the sensor is used to recognize a type of exercise, a frequency of exercise, or a weight of exercise performed by the user.

In detail, the measurement unit 311 may include a geomagnetic sensor used to sense a direction and position of a weight portion or the user's body, for example, a wrist. Also, the measurement unit 311 may include an acceleration sensor used to sense an acceleration value needed to measure a movement direction and velocity of an exercise machine. Also, the measurement unit 311 may include a gyro sensor used to sense a rotation angle, a position, and a direction of a weight portion or the user's body, for example, a wrist.

In other words, the measurement unit 311 may include various sensors such as a geomagnetic sensor, an acceleration sensor, a gyro sensor, etc. The sensors of the measurement unit 311 may be attached on the weight portion 190 of the fitness structure 100 of FIG. 6, or may be included in a terminal such as a smart phone or a wearable device carried by the user.

The analysis unit 313 analyzes a type, weight, or frequency of exercise from the measured value extracted from the measurement unit 311, under the control of the controller 309.

Figure 16:
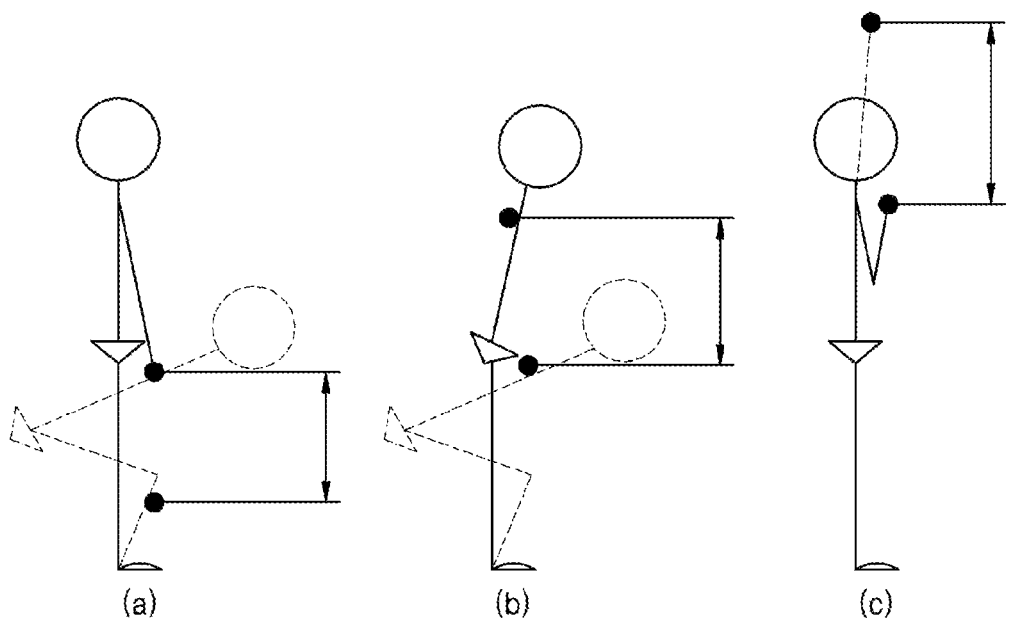
FIG. 16 illustrates movement paths of a bar when a squat, a dead lift, and an overhead press are performed.

For example, during training using a barbell, a type of exercise may be estimated from a movement path of a bar, a cable, or a load portion. For example, as illustrated in FIG. 16, an exercise path varies when a squat, a dead lift, or an overhead press is performed. Accordingly, by analyzing various pieces of data measured by the measurement unit 311, the type, frequency, or weight of exercise performed by the user may be checked.

The user approval unit 315 may approve the identity of a user who currently uses the fitness structure 100 of FIG. 6, under the control of the controller 309 and provide a result of the analysis of the analysis unit 313 to each user. In other words, when the user inputs a certain ID and/or password through the input/output unit 305, the user approval unit 315 approves the identity of a user who currently uses the fitness structure 100 of FIG. 6 from the input ID and/or password. As a result, an exercise result may be analyzed or stored for each user and thus an exercise history of a user may be provided to the user. Also, an advertisement that is personalized for each user may be displayed.

According to the fitness structure of the present inventive concept, space usability may be improved and various exercises may be performed with a single structure.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

REFERENCE NUMERALS

100: fitness structure
110: frame
120: bar
131: first cable
132: second cable
140: load portion
150: support portion
160: support member
170: catcher bar
180: catcher bar support portion
190: weight portion

What is claimed is:
1. A fitness structure comprising:
a bar having a first end portion and a second end portion;
a bar support frame provided at each side of the bar and the bar support frame having a plurality of bar holders to place the bar at a plurality of heights;
a first load and a second load spaced apart from the bar to a certain degree and facing each other;
a first cable coupled between the first end portion of the bar and the first load; and
a second cable coupled between the second end portion of the bar and the second load,
wherein heights of the first load and the second load vary depending on a height of one of the plurality of bar holders at which the bar is detachably placed,
wherein the heights of the first load and the second load have a predetermined distance from a ground when no external force is applied to the first cable and the second cable,
wherein, when the bar is in use, the bar is held by a user and physically detached from the one of the plurality of bar holders, and when the bar is placed on the one of the plurality of bar holders, one or more weight portions are attachable and detachable with respect to the first load and the second load,
wherein in a state in which the bar placed on the one of the plurality of bar holders is detached from the one of the plurality of bar holders and held by the user, the bar is capable of performing a downward motion in the direction of gravity from a height of the one of the plurality of bar holders while the first cable is coupled between the first end portion of the bar and the first load, and the second cable is coupled between the second end portion of the bar and the second load, and
wherein a bar accommodation frame is defined in a lower portion of the bar support frame and in a state in which the bar is accommodated in the bar accommodation frame, the bar is capable of performing an upward motion in a direction opposite to gravity.

2. The fitness structure of claim 1, wherein the one or more weight portions are detachably provided on the first load and the second load, regardless of positions of the first load and the second load.

3. The fitness structure of claim 1, wherein an insertion hole is formed in the bar support frame at each of the plurality of heights, each of the plurality of bar holders is inserted into the insertion hole, and the bar is supported by the plurality of bar holders.

4. The fitness structure of claim 1, wherein, as the bar is supported by the one of the plurality of bar holders, even when the bar is supported on any one of the plurality of bar holders, the one or more weight portions are detachably provided to the first load and the second load.

5. The fitness structure of claim 1, wherein the first load and the second load are moved in a same direction as a movement direction of the bar in a third direction.

6. The fitness structure of claim 5, wherein, when the bar is moved in a direction ascending from the ground, the first load or the second load is ascended in a vertical direction by the first cable and the second cable connected to the bar.

7. The fitness structure of claim 6, wherein a movement distance of the bar in the third direction is longer than a movement distance of the first load or the second load in the third direction.

8. The fitness structure of claim 1, wherein a distance sensor measuring a movement distance of the first load or the second load is further provided on the first load or the second load.

9. The fitness structure of claim 1, wherein each of the first load and the second load comprises:

a guide frame extending in one direction;

an elevation frame elevating along the guide frame; and a weight coupling frame protruding from the elevation frame to allow the one or more weight portions to be coupled to the weight coupling frame.

10. The fitness structure of claim 9, wherein the weight coupling frame of the first load and the weight coupling frame of the second load protrude in directions facing each other.

11. The fitness structure of claim 1, further comprising a frame on which the first load, the second load, the first cable, and the second cable are provided and having an inner space formed in the frame, wherein one or more weight support portions on which the one or more weight portions are supported is formed on the frame, and the one or more weight support portions protrude from the frame inwardly toward the inner space of the frame.

12. The fitness structure of claim 11, wherein one or more pulleys are formed on the frame, the first cable, the first load, and the one or more pulleys constitute a pulley system, and the second cable, the second load, and the one or more pulleys constitute a pulley system.

13. The fitness structure of claim 1, wherein the user is positioned between the first cable and the second cable.

14. A fitness structure comprising:

a bar having a first end portion and a second end portion;

a bar support frame provided at each side of the bar and having a plurality of bar holders to place the bar at a plurality of heights;

a first cable coupled to the first end portion of the bar;

a second cable coupled to the second end portion of the bar; and one or more loads connected to the first cable or the second cable and applying a certain load to the bar, wherein the one or more loads comprise a first load and a second load, which are at each side of the bar to face each other, each of the first load and the second load comprises:

a guide frame extending in one direction;

an elevation frame elevating along the guide frame; and a weight coupling frame protruding from the elevation frame to allow one or more weight portions to be coupled to the weight coupling frame, and the weight coupling frame of the first load and the weight coupling frame of the second load protrude in directions facing each other, wherein heights of the first load and the second load vary depending on a height of one of the plurality of bar holders at which the bar is detachably placed, wherein the heights of the first load and the second load have a predetermined distance from a ground when no external force is applied to the first cable and the second cable, wherein, when the bar is in use, the bar is held by a user and physically detached from the one of the plurality of bar holders, and when the bar is placed on the one of the plurality of bar holders, one or more weight portions are attachable and detachable with respect to the first load and the second load, wherein in a state in which the bar placed on the one of the plurality of bar holders is detached from the one of the plurality of bar holders and held by the user, the bar is capable of performing a downward motion in the direction of gravity from a height of the one of the plurality of bar holders while the first cable is coupled between the first end portion of the bar and the first load, and the second cable is coupled between the second end portion of the bar and the second load, and wherein a bar accommodation frame is defined in a lower portion of the bar support frame and in a state in which the bar is accommodated in the bar accommodation frame, the bar is capable of performing an upward motion in a direction opposite to gravity.

15. The fitness structure of claim 14 wherein the one or more loads are moved in a same direction as a movement direction of the bar in a third direction.

16. The fitness structure of claim 15, wherein, when the bar is moved in a direction ascending from the ground, the one or more loads are ascended in a vertical direction by the first cable and the second cable connected to the bar.

17. The fitness structure of claim 15, wherein a movement distance of the bar in the third direction is longer than a movement distance of the one or more loads in the third direction.

18. The fitness structure of claim 14, wherein the one or more weight portions are coupled to the weight coupling frame of the first load or the second load, regardless of a position of the first load or the second load.

19. The fitness structure of claim 14, further comprising a frame on which the first load, the second load, the first cable, and the second cable are provided and having an inner space formed in the frame, wherein one or more weight support portions on which the one or more weight portions are supported is formed on the frame, and the one or more weight support portions protrude from the frame inwardly toward the inner space of the frame.

20. The fitness structure of claim 19, wherein one or more pulleys are formed on the frame, the first cable, the first load, and the one or more pulleys constitute a pulley system, and the second cable, the second load, and the one or more pulleys constitute a pulley system.

* * * * *